US00PP32945P3

(12) United States Plant Patent
Beckman

(10) Patent No.: US PP32,945 P3
(45) Date of Patent: Mar. 30, 2021

(54) CALLA LILY PLANT NAMED 'CAPITOLA'

(50) Latin Name: *Zantedeschia sprengeri*
Varietal Denomination: Capitola

(71) Applicant: Dümmen Group B.V., De Lier (NL)

(72) Inventor: Peter Beckman, Santa Cruz, CA (US)

(73) Assignee: Dümmen Group B.V., De Lier (NL)

( * ) Notice: Subject to any disclaimer, the term of this patent is extended or adjusted under 35 U.S.C. 154(b) by 0 days.

(21) Appl. No.: 16/602,418

(22) Filed: Oct. 1, 2019

(65) Prior Publication Data

US 2020/0113104 P1 Apr. 9, 2020

Related U.S. Application Data

(60) Provisional application No. 62/766,205, filed on Oct. 4, 2018.

(51) Int. Cl.
*A01H 6/10* (2018.01)
*A01H 5/02* (2018.01)
*A01H 6/56* (2018.01)

(52) U.S. Cl.
USPC ..... Plt./490
CPC ..... *A01H 6/56* (2018.05)

(58) Field of Classification Search
USPC ..... Plt./490
CPC ..... A01H 6/10; A01H 5/02
See application file for complete search history.

*Primary Examiner* — Keith O. Robinson
(74) *Attorney, Agent, or Firm* — The Webb Law Firm

(57) ABSTRACT

'Capitola' is a new variety of calla lily plant having red-purple colored spathes that are positioned above the foliage. The flower stems are strong and long lasting. The leaves are green with no maculations present.

1 Drawing Sheet

Botanical classification: *Zantedeschia sprengeri*.
Varietal denomination: 'Capitola'.

BACKGROUND OF THE NEW PLANT

The present invention comprises a new and distinct cultivar of calla lily, botanically known as *Zantedeschia sprengeri* and hereinafter referred to by the cultivar name 'Capitola'.

'Capitola' is a product of a planned breeding program having the objective of creating *Zantedeschia* varieties for pot flower production in a wide range of colors and classic flower shapes. 'Capitola' was selected in 2008 in Moss Landing, Calif. as an inbred seedling selected from an open-pollinated population and self-pollinated for many generations. As such, its exact parentage is unknown and comparisons thereto cannot be provided.

The new variety was first asexually reproduced through tissue culture shoot propagation in October of 2011 in Moss Landing, Calif. Asexual reproductions of 'Capitola' have demonstrated that the combination of characteristics as herein disclosed for the new variety are retained and reproduced true to type through successive generations of asexual reproduction.

The following observations, measurements and comparisons describe plants grown in 15 cm pots at 65 days from planting in 't Zand, The Netherlands under greenhouse conditions which approximate those generally used in horticultural practice. Color references are made to The 2001 R.H.S. Colour Chart of The Royal Horticultural Society of London, 4$^{th}$ Edition, except where general color terms of ordinary significance are used.

The present invention has not been evaluated under all possible environmental conditions. The phenotype may vary with variations in environment without a change in the genotype of the plant.

The following traits have been repeatedly observed and determined to be basic characteristics of 'Capitola' which, in combination, distinguish this calla lily as a new and distinct cultivar:

1. Red-purple colored spathes;
2. Inflorescences are positioned above the foliage; and
3. Firm, long-lasting peduncles.

Table 1 provides a comparison of 'Capitola' to similar *Zantedeschia sprengeri* varieties 'Garnet Glow' (unpatented), 'California Red' (unpatented), and 'Flirt' (unpatented).

TABLE 1

| Comparison variety | Differing trait(s) | Comparison expression | Present variety expression |
|---|---|---|---|
| 'Garnet Glow' | Peduncle strength | Early flower nodding | Erect peduncles with no nodding observed at 21 days |
| 'California Red' | Spathe color | Red Group RHS 46A | Between Red-Purple Group RHS 59A-59B |
| | Flowering time | 78 days to flower | 68 days to flower |
| 'Flirt' | Leaf maculations | Present | None present |

BRIEF DESCRIPTION OF THE DRAWING

The accompanying photographic drawing illustrates the new variety at 65 days from planting, with the colors being as nearly true as is possible with color illustrations of this type.

DESCRIPTION OF THE NEW PLANT

Type: Deciduous.
Form: Semi-spreading.

Average spread: 40-49 cm.
Branch number: Average.
Branch color: Yellow-Green Group RHS 145A to 145B.
Height of leaf canopy above the soil: 24-29 cm.
Height of top of inflorescences above the soil: 36-42 cm.
Number of inflorescences per tuber:
18-20 *cm in diameter.*—7-13.
Lastingness of inflorescences on the plant: About 14 days.
Main use: Potted plant.
Average time of flowering: Tubers planted in the field in May in 't Zand, The Netherlands bloom in July. Tubers planted in a greenhouse in February in 't Zand, The Netherlands bloom in April.
Disease/pest resistance: Moderate tolerance to Pythium root rot and Erwinia bulb soft rot.
Hardiness: Not tested.
Leaves:
*Number per plant.*—23-51.
*Width.*—4.5-7 cm, with broadest position in the middle.
*Length.*—23-30 cm.
*Shape.*—Lanceolate.
*Apex.*—Apiculate.
*Base.*—Attenuate.
*Margin.*—Entire.
*Color.*—Upper surface: Green Group RHS 137B to 137C, with no maculations present. Lower surface: Green Group RHS 143A to 143B, with no maculations present.
*Surface texture.*—Smooth (both surfaces).
*Leaf venation.*—Pattern: Pinnate. Color: Yellow-Green Group RHS 144A to 144B.
*Lobes.*—None present.
*Petiole.*—Length: 23-28 cm. Diameter: 12-15 mm. Texture: Smooth. Shape: Cylindrical. Strength: Medium. Color: Upper surface: Green Group RHS 143B to 143C. Lower surface: Yellow-Green Group RHS 144C to 144D.
Spathe:
*Position.*—Above the foliage.
*Length.*—4.5-7 cm.
*Width.*—4-5 cm.
*Fragrance.*—None.
*Shape.*—Leaf-like.
*Texture.*—Smooth.
*Apex.*—Apiculate.
*Base.*—Amplexicaul.
*Margin.*—Entire.
*Color.*—Throat spot: Red-Purple Group RHS 72B. Upper surface: Red-Purple Group RHS 71A to 71B. Lower surface: Red-Purple Group RHS 70B to 70C.
Spadix:
*Length.*—25-40 mm.
*Diameter.*—8-11 mm.
*Color.*—Yellow Group RHS 13B to 13C.
*Position relative to spathe.*—Upright from base.
*Apex.*—Rounded and Yellow Group RHS 4C to 4D.
*Pollen amount.*—Abundant.
Peduncle:
*Strength.*—Strong and erect, with no nodding observed until day 21.
*Length.*—37-43 cm.
*Diameter.*—11-17 mm.
*Texture.*—Smooth.
*Color.*—Base: Yellow-Green Group RHS 144C to 144D. Upper portion: Yellow-Green Group RHS 144A to 144B.
Seeds:
*Number/flower.*—17.
*Length.*—3.7-5.8 mm.
*Diameter.*—2.5-5.1 mm.
*Color.*—White Group RHS 155C.
Reproductive organs:
*Anther.*—Shape: Round. Length: Less than 1 mm. Color: Yellow Group RHS 8C to 8D.
*Filament.*—Length: Less than 1 mm. Color: White Group RHS 155D.
*Style.*—Length: Less than 1 mm. Color: Yellow Group RHS 8C to 8D.
*Pistil.*—Number: 15-30. Length: About 1 mm.
*Stigma.*—Shape: Round. Length: Less than 1 mm. Diameter: Less than 1 mm.
*Ovaries.*—Texture: Smooth. Length: Varies between 1 to 10 mm. Diameter: Varies between 1 to 10 mm. Color: Top: Yellow Group RHS 8A to 8B. Bottom: Red-Purple Group RHS 62A to 62B.

I claim:

1. A new and distinct variety of calla lily plant named 'Capitola' as herein described and illustrated.

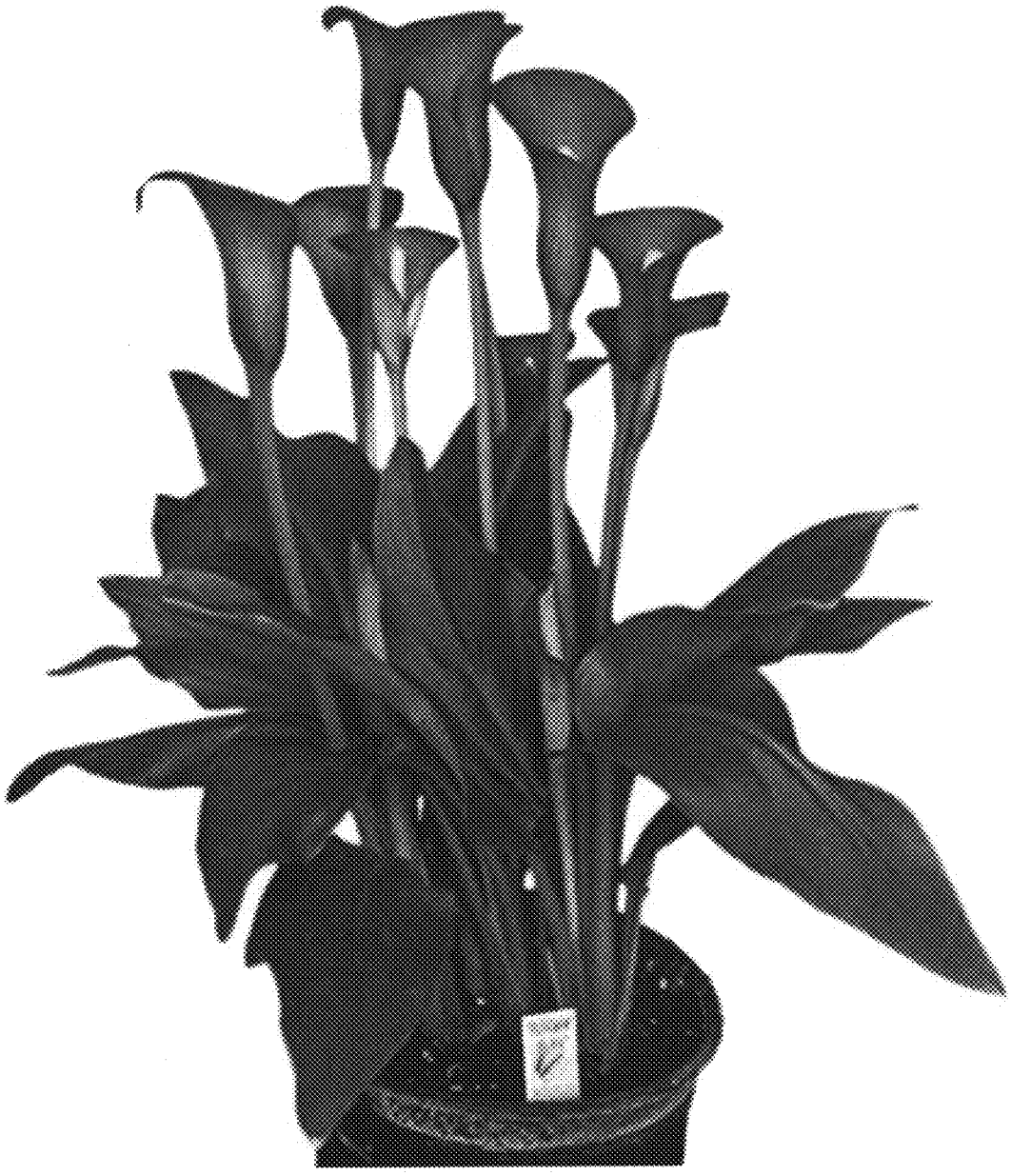

* * * * *